(12) United States Patent
Chung et al.

(10) Patent No.: US 8,758,822 B2
(45) Date of Patent: Jun. 24, 2014

(54) METHOD FOR MANUFACTURING UNIFORM SIZE POLYMERIC NANOPARTICLES CONTAINING POORLY SOLUBLE DRUGS

(75) Inventors: Bong Hyun Chung, Daejeon (KR); Yong Taik Lim, Daejeon (KR); Jung Hyun Han, Nonsan-si (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 12/990,540

(22) PCT Filed: Apr. 30, 2009

(86) PCT No.: PCT/KR2009/002289
§ 371 (c)(1),
(2), (4) Date: Jan. 10, 2011

(87) PCT Pub. No.: WO2009/134091
PCT Pub. Date: Nov. 5, 2009

(65) Prior Publication Data
US 2011/0171269 A1  Jul. 14, 2011

(30) Foreign Application Priority Data
May 1, 2008  (KR) .................. 10-2008-0041017

(51) Int. Cl.
| | | |
|---|---|---|
| *A61K 9/14* | (2006.01) | |
| *A61K 38/00* | (2006.01) | |
| *A61K 38/36* | (2006.01) | |
| *A61K 38/13* | (2006.01) | |
| *A01N 45/00* | (2006.01) | |
| *A61K 31/56* | (2006.01) | |
| *A61K 31/585* | (2006.01) | |
| *A61K 31/54* | (2006.01) | |
| *A61K 31/505* | (2006.01) | |
| *A61K 31/095* | (2006.01) | |
| *A61K 31/045* | (2006.01) | |
| *B01D 61/00* | (2006.01) | |
| *A61K 9/16* | (2006.01) | |
| *C08J 3/03* | (2006.01) | |
| *B01D 65/00* | (2006.01) | |

(52) U.S. Cl.
CPC .......... *A61K 9/1652* (2013.01); *C08J 3/03* (2013.01); *B01D 65/00* (2013.01); *Y10S 516/929* (2013.01)
USPC .......... 424/489; 514/3.3; 514/12.2; 514/14.9; 514/19.3; 514/20.5; 514/26; 514/169; 514/175; 514/225.2; 514/269; 514/706; 514/730; 516/929; 210/651

(58) Field of Classification Search
None
See application file for complete search history.

(56) References Cited

U.S. PATENT DOCUMENTS

| | | | |
|---|---|---|---|
| 5,540,937 A | 7/1996 | Billot et al. | |
| 6,322,805 B1 * | 11/2001 | Kim et al. | .............. 424/426 |
| 2005/0287196 A1 | 12/2005 | Cho et al. | |

FOREIGN PATENT DOCUMENTS

| | | |
|---|---|---|
| JP | 6-87758 A | 3/1994 |
| JP | 10-511957 A | 11/1998 |
| JP | 11-504655 A | 4/1999 |
| JP | 2007-509136 A | 4/2007 |
| JP | 2009-533453 A | 9/2009 |
| KR | 10-0210510 B1 | 4/1999 |
| KR | 10-2002-0000698 A | 1/2002 |
| KR | 10-2005-0038224 A | 4/2005 |
| KR | 10-2005-0093236 A | 9/2005 |
| KR | 10-0722607 B1 | 5/2007 |
| WO | 96/20698 A2 | 7/1996 |
| WO | 97/02022 A1 | 1/1997 |
| WO | 2005/037249 A1 | 4/2005 |
| WO | 2008/051291 A2 | 5/2008 |

OTHER PUBLICATIONS

Astete et al.; J. Biomater. Sci. Polymer Ed.; vol. 17, No. 3, pp. 247-289 (2006).*
Machine Translation of IDS reference KR 10-2005-0093236 (Park et al.; pub'd Sep. 23, 2005).*
Tewes, et al., "Comparative study of doxorubicin-loaded poly(lactide-co-glycolide) nanoparticles prepared by single and double emulsion methods", European Journal of Pharmaceutics and Biopharmaceutics, 66, 2007, pp. 488-492.
Kim, et al., "Design and Gastrointestinal Permeation of Non-aqueous Biphenyl Dimethyl Dicarboxylate Oral Liquid Preparations", J. Kor. Pharm. Sci., vol. 30, No. 2, 2000, pp. 119-125.
Khang, et al., "Recent development trends of the improving bioavailability by polymeric nanovehicles of poorly fiater-soluble drugs", Polymer Science and Technology, vol. 13, No. 3, Jun. 2002, pp. 342-359.

* cited by examiner

*Primary Examiner* — Jeffrey T Palenik
(74) *Attorney, Agent, or Firm* — Lucas & Mercanti, LLP (57) ABSTRACT

The present invention relates to a method for manufacturing uniform size polymeric nanoparticles containing poorly soluble drugs, and more particularly, to a method for manufacturing uniform size polymeric nanoparticles containing poorly soluble drugs, including a first step of dissolving a biodegradable polymer in a non-volatile polar organic solvent, a second step of adding poorly soluble drugs to water and the biodegradable polymer solution to produce a dispersion, and a third step of adding the dispersion to emulsifier solutions in a batch under the condition of low mechanical energy level stirring. The polymeric nanoparticles of the present invention is capable of manufacturing nano-sized small and uniform polymeric nanoparticles through a simple method of employing a non-volatile polar solvent, especially a solvent having a polarity similar to that of water, as a solvent for a mixture solution of biodegradable polymer and poorly soluble materials, and using a low mechanical energy condition and batch-adding of dispersion in an emulsifying process. The polymeric nanoparticles of the present invention are advantageous in that the dissolution rate of the poorly soluble drugs contained in polymeric particles is dramatically improved, and the poorly soluble drugs are gradually and steadily released and maintained at a constant density over a long period of time.

6 Claims, 7 Drawing Sheets

METHOD FOR MANUFACTURING UNIFORM SIZE POLYMERIC NANOPARTICLES CONTAINING POORLY SOLUBLE DRUGS

CROSS-REFERENCE TO RELATED APPLICATIONS

This application is a 371 of PCT/KR2009/002289 filed on Apr. 30, 2009, which claims the benefit of Korean Application No. 10-2008-0041017 filed on May 1, 2008, the contents of each of which are incorporated herein by reference.

TECHNICAL FIELD

The present invention relates to a method for manufacturing uniform size polymeric nanoparticles containing poorly soluble drugs.

BACKGROUND ART

When drugs are administered for treatment, active ingredients are delivered via physiochemically designed systems to maximize the treatment effect and to suit the convenience of patients. These systems are called dosage forms which include injections, capsules and tablets.

Administered drugs pass through many biomembranes and organs to finally reach target organs. The drug reached the target organ combines with receptors distributed over the organ to realize pharmaceutical effects. After then, the drug is metabolized by liver and other organs and released out of body with stool and/or urine. The problem is, however, it is usually difficult to control the process of delivering drugs to the target area, and the efficiency of delivery is usually low. Hence, to obtain an optimal effect and safety, it is necessary to control the in vivo behavior of drugs from the moment of administration until excretion to accomplish a selective delivery to the target area by employing a variety of methods. The system of the above control is called drug delivery system which has been extensively studied. (Galenical pharmacy-pharmaceutics, Pharmaceutics subcommittee, Committee of Colleges of Pharmacy of Korea, p 483, 2000)

Some of the drug delivery systems adopt manufacturing methods taking Advantage of nano- or micro-size particles which can deliver drugs impregnated or capsulized inside the polymer by using biodegradable polymer, and of emulsifiers. The method of using emulsifier is to prepare polymeric particles by redispersing a dispersion inside an emulsifier solution wherein active ingredients and polymer are mixed and dissolved in an organic solvent. As polymers in the dispersion is hydrophobic, they can combine with the hydrophobic parts of emulsifiers resulting in formation of dispersed globular shaped particles whose sizes tend to decrease through intensive stirring or the strength of vibration. A manufacturing method using emulsifiers has been reported; doxorubicin and poly-D,L-lactic acid-co-glycolic acid (PLGA) which are anticancer agents are dissolved in methylenechloride solution to form an oil phase, which is added into the 3% of poly vinylalcohol solution under the condition of a strong vibration of ultrasound to finally prepare PLGA nanoparticles containing doxorubicin which has an average size of less than 500 nm (Tewes F et al., European Journal of Pharmaceutics and Biopharmaceutics 66:488492, 2007). However, the manufacturing methods of nonoparticles using emulsifiers have disadvantages; when ultrasound is applied, yield of nanoparticle is good but the operation cost increases because strong energy is required; and when stirring method is employed, high mechanical energy is required for the high rotational speed. Another drawback is that this method requires adjusting the speed of adding polymer-drug. Moreover, when volatile solvents having low boiling points are used, solvent recovery apparatuses are required to avoid risks involved, and the yield of nanoparticles decreases due to the extensive and/or uneven distribution of particles. To solve these problems, a process to manufacture nanoparticles having comparatively even distribution and high yield even under the low mechanical energy setting has been greatly needed.

Patients with chronic diseases are required to take poorly soluble drugs containing poorly soluble materials as active ingredients over a long period of time. This means a single intake of even a slightly heavy dose may result in side effects due to in vivo accumulation of the drug over a long period of time. With poorly soluble drugs, patients with chronic diseases should take heavy dose each time because of the low dissolution rate, which should be desperately improved to prevent side effects. In addition, to avoid inconveniences of multiple daily intakes of drugs over a long period of time, it is preferred to develop a gradually and steadily releasing dosage form which can reduce the frequency of intake and maintain a constant blood concentration over a long period of time.

For example, biphenyl-dimethyl-dicarboxylate (BDD) drugs are used to treat hepatitis and protect liver, and clinically to inhibit activities of serum transaminase, especially Serum glutamic pyruvic transaminase (SGPT) (Hyo-Seok Lee and others, The Korean Journal of Internal Medicine, vol. 40, No. 2, 1991). Animal tests have also shown that BDDs protect liver from the damage caused by toxicity of carbon tetrachloride or thioacetamide, and increase activities of cytochrome $P_{450}$ 2B1 mRNA and benzyloxyresorufin-O-dealkylase in addition to removing free radicals.

Above compounds, however, have so poor solubility in water (2.0-4.0 μg/ml) and low dissolution rate that their bioavailability is no more than 20-30% when taken as a form of tablet. (Kim H J et al., J Kor Pharm Sci Vol. 30, No. 2:119-125, 2000). Consequently, it is a demerit of liver treatment agents of BDDs; when they are administered as a form of tablet, heavy and continuous intakes are required due to the low in vivo dissolution rate and bioavailability.

On the other hand, extensive studies are in progress to enhance dissolubility of poorly soluble drugs via physical or chemical reformation and especially, studies on enabling oral intake of poorly soluble drugs via physical reformation of drug crystals by using the nanoparticle process are under way. (Khang K S et al., Polymer Science and Technology 13(3) 342-359, 2002). In addition, a variety of experiments have been reported enhancing bioavailability and duration of drug effects by containing drugs in biodegradable polymeric particles.

For example, Korea Patent 2005-0038224, "Oral microemulsion composition comprising biphenyldimethyldicarboxylate and carduus marianus extract or silybin isolated therefrom," discloses cases of better treatment effects on (chronic) liver diseases by virtue of enhanced bioavailability upon adding additives (co-surfactant, surfactant and oil) on the poorly soluble drugs to increase the dissolution rate.

Another Korea Patent 1997-0058726 discloses a water soluble protein-containing drug evenly distributed on a biodegradable polymer, a sustained release dosage form which improves excessive release in early stage of intake by coating the water soluble protein-containing drugs with drug particles or a biodegradable polymer matrix which are biocompatible and hydrophobic. But the dissolution rate and sustained release effects still fall short of expectations.

Thus, the present inventors have developed an original technology capable of manufacturing polymeric nanoparticles containing poorly soluble materials which are evenly distributed; by dissolving a poorly soluble materials in a biodegradable polymer solution which is dissolved in a non-volatile polar organic solvent especially in a highly hydrophilic organic solvent; and by coating with an emulsifier under the condition of low mechanical energy level stirring. The polymeric nanoparticles agent containing poorly soluble materials of the present invention may enhance bioavailability by increasing dissolution rate of poorly soluble drugs, and maintain a constant blood concentration over a long period of time, and reduce the dosage compared with the conventional poorly soluble drugs, thereby leading to completion of the present invention.

DISCLOSURE OF INVENTION

Technical Problem

An object of the present invention is to provide a method of manufacturing nanoparticles having a narrow size-distribution. In order to achieve the object, the present invention provides a method of manufacturing polymeric nanoparticles including a first step of dissolving a biodegradable polymer in a non-volatile polar organic solvent, a second step of adding poorly soluble drugs to water and the biodegradable polymer solution to produce a dispersion, and a third step of adding the dispersion to emulsifier solutions in a batch under the condition of low mechanical energy level stirring.

Technical Solution

According to the present invention, the polymeric nanoparticles of the present invention are capable of manufacturing nano-sized small and uniform polymeric nanoparticles using a low mechanical energy condition of stirring.

Advantageous Effects

The polymeric nanoparticles of the present invention are advantageous in that the dissolution rate of the poorly soluble drugs contained in polymeric particles is dramatically improved, and the poorly soluble drugs are gradually and steadily released and maintained at a constant density over a long period of time and consequently, the drug consumption may be reduced.

BEST MODE

Hereinafter, the present invention will be described in detail.

The present invention provides a method of manufacturing uniform size polymeric nanoparticles containing poorly soluble drugs, including a first step of dissolving a biodegradable polymer in a non-volatile polar organic solvent, a second step of adding poorly soluble drugs to water and the biodegradable polymer solution to produce a dispersion, and a third step of adding the dispersion to emulsifier solutions in a batch under the condition of low mechanical energy level stirring.

Hereinafter, the present invention will be described in detail by step.

The first step is dissolving a biodegradable polymer in a non-volatile polar organic solvent.

The biodegradable polymer is a biocompatible polymer which can be dissolved in the body. More particularly, one of or a mixture of polyester-based polymers such as poly-L-lactic acid (PLA), poly glycolic acid (PGA), poly-D-lactic acid-co-glycolic acid (PLGA), poly-L-lactic acid-co-glycolic acid, poly-D,L-lactic acid-co-glycol acid, poly-caprolactone, poly-valerolactan, poly-hydroxy butyrate and poly-hydroxy valerate may be used but not be limited thereto. Especially; it is more desirable to use PLGA from the perspective of biodegradability and biocompatibility. Above-mentioned PLGA is a medically approved polymer by FDA, U.S., and free from toxicity to be more conveniently used than other polymers for medical applications such as a drug delivery agent or a biomaterial. Furthermore, PLGA is characterized to adjust the drug release behavior by changing the degrading speed of the polymers in accordance with the adjustment of fraction or molecular weight of glycolide and lactide when copolymerized. (Anderson J M et al., Advanced Drug Delivery Reviews 28:5-24, 1997).

Organic solvent of the first step above is preferably a non-volatile polar solvent, and more preferably, a highly hydrophilic solvent which has a similar polarity to water. For example, one of or a mixture of non-volatile solvents such as dimethyl sulfoxide (DMSO), dimethyl formamide (DMF), Dimethyl acetamide (DMAc), N-methyl-2-pyrrolidone (NMP), pyrrolidone, 1,3-Dimethyl-3,4,5,6-tetrahydro-2 (1H)-pyrimidinone (DMPU), hexamethylphosphoramide (HMPA) may be used but not be limited thereto. Among those, DMAc is more preferable.

The second step is adding poorly soluble drugs to water and then, adding them to the biodegradable polymer solution to produce a dispersion.

Above poorly soluble drugs to water may be used without specific restrictions if the drug controls bioavailability as dissolution of the drug becomes the rate determining step due to low solubility. Furthermore, above drugs may be used as either oil phase or crystal phase. More particularly, the following may be used: griseofulvin, digoxin, dipyridamole, spironolactone, cyclosporin, amphotericin B, fluorouracil, etoposide, 6-mercaptopurine, dexamethasone, perphenasine, biphenyl-dimethyl-dicarboxylate (BDD), a poorly soluble liver disease treatment agent and dimethyl dimethoxy biphenyl dicarboxylate (DDB).

According to the second step, a dispersion containing poorly soluble drugs in an oil or crystal phase and the polymeric solution prepared in the first step may be produced.

The ratio between the above poorly soluble drugs and biodegradable polymer is preferably at 0.5-5:10-100 on a part by weight basis.

The third step is adding the dispersion produced in the second step on emulsifier solutions in a batch under the condition of low mechanical energy level stirring.

Emulsifiers used in the third step may be any amphipathic (possessing both hydrophobic and hydrophilic elements) solvent which can disperse an oil phase in aqueous solutions. Preferably, propylene glycol (1,2-dihydroxypropane), polyethylene glycol (especially, polyethylene glycol with molecular weight of 200 to 600 (PEG)), propylene carbonate (4-methyl-2-oxo-1,3-dioxolane), polyvinyl alcohol (PVA), poly vinyl pyrrolidone (PVP) may be used but not be limited thereto. The emulsifier aqueous solution is prepared by dissolving above emulsifiers in the Milli-Q distilled water, and especially PVA solution or PVP solution is desirable.

In the above third step, the dispersion produced in the second step is added to emulsifier solutions in a batch under the condition of low mechanical energy level stirring, preferably at 50-5000 rpm and more preferably, at 100-1000 rpm. As a result, a dispersion with dispersed biodegradable polymeric nanoparticles that poorly soluble drugs are impregnated is produced. At this moment, as the solvent of the above dispersion has a polarity similar to water to be highly hydrophilic, the solvent diffuses rapidly and then, becomes stabilized by the emulsifier, and finally uniform size polymeric nanoparticles may be formed. Upon removing emulsifiers, organic solvents and distilled water from above polymeric nanoparticles solution by using a filtration device such as a separation membrane filtration device, and simultaneously concentrating polymeric nanoparticles that poorly soluble drugs are impregnated, the biodegradable polymeric nanoparticles containing poorly soluble drugs may be obtained. The manufacturing method of the present invention reduces operation costs because stirring is carried out under a low mechanical energy level. In addition, uniform size polymeric nanoparticles may be obtained.

The biodegradable polymeric nanoparticles have a deviation in size of 0~30 nm, more preferably 5~25 nm, and an average size of 200 nm or less (Refer to FIGS. 1 to 5 and Table 1).

In addition, these nanoparticles agents provide prolonged pharmaceutical effects for 2 weeks or more as shown in Examples. Treatment results of oral intake of nanoparticles containing active ingredients against carbon tetrachloride-induced liver damage were compared with those of oral intake of active ingredients only. After a 4-week session of oral intake, the combination of nanoparticles and active ingredients showed a little lower but similar treatment effects compared with active ingredients-only. However, when the combination and the active ingredients-only were independently administered for 2 weeks and a continuous liver damage was conducted, the protective effects of the combination lasted for 4 weeks (Refer to Tables 2 and 3) but those of active ingredients-only declined gradually for a while and decreased sharply in the 4$^{th}$ week. (Refer to FIGS. 6 and 7). Consequently, the sustained solubility and the sustainability of the nanoparticles of the present invention were confirmed with the duration of over 2 weeks.

In addition, as shown in the table 2 and 3, the inhibiting effect of the BDD and BDD-containing polymeric nanoparticles administration group on increase of carbon tetrachloride-induced ALT and AST concentration were roughly 2 times or more. The effect of BDD-containing polymeric nanoparticles administration group of the Example 2 was numerically a little lower than that of the BDD administration group but similar. On the other hand, the total administration amount of BDD-containing polymeric nanoparticles of the Example 2 was 25 mg including 2.5 mg of BDD, which means the drug dosage accounts for 1/10 of the Group 2 which administered 25 mg of BDD. Examining the results of the Group 3 against the Example 2, it is understood that with the 1/10 of drug dosage of the Group 2, the effects ratio against the Group 2 reached about 56% (Table 1) and about 91% (Table 2), which means an actual dissolution rate was improved by 5.6 times and 9.1 times, respectively.

In summary, compared with BDD-only administration, the biodegradable polymeric nanoparticles containing poorly soluble drugs of the present invention provide more prolonged pharmaceutical effects with a less dosage per administration.

Mode for the Invention

Hereinafter, the present invention will be described in more detail with reference to following examples. However, the following examples are provided for illustrative purposes only, and the scope of the present invention should not be limited thereto in any manner.

Example 1

Preparation of PLGA-BDD Nanoparticles Using DMAc 10 g of PLGA(poly-D-lactic acid-co-glycolic acid; Boehringer Ingelheim, Germany) was dissolved in 300 ml of Dimethyl acetamide (DMAc), and 1 g of BDD (biphenyl-dimethyl-dicarboxylate) was added and dissolved to prepare a dispersion. Above PLGA-BDD dispersion was added on the 3 l of 4%-PVA (polyvinyl alcohol; Sigma-Aldrich, USA) emulsifier solution in a batch under the condition of low mechanical energy level stirring of 500 rpm for 3 hours.

After then, the nanoparticles solution was stirred in a container by using a pump-type separation membrane filtration device (Labscale™ TFF System, Millipore, USA) and circulated through a separation pipe by a circulation pump to rapidly remove the emulsifier, the organic solvent and distilled water through a separation membrane filter (Pellicon XL Filter, 500K; Millipore, USA) of the separation membrane, and to concentrate the nanoparticles in a continuous-circulatory concentration manner. Separated and concentrated nanoparticles were frozen dried (EYELA, Japan) to obtain powder of the particles, and kept at 4° C.

Upon observing the finally obtained nanoparticles through SEM (Sirion, Japan), TEM (JEOL, Japan) and a particle size analyzer (OTSUKA ELECTRONICS, Japan), uniform PLGA-BDD nanoparticles containing active ingredients having narrow bounds of particles distribution and 142 nm of average particle diameter were confirmed. (Refer to Table 1, FIGS. 1 to 3).

Example 2

Preparation of PLGA-BDD Nanoparticles Using DMSO 100 mg of PLGA was dissolved in 3 ml of DMSO, and 10 mg of BDD was added on it and was dissolved to prepare a dispersion. The above PLGA-BDD dispersion was added on the 30 ml of 4%-PVA emulsifier solution in a batch under the condition of low mechanical energy level stirring of 500 rpm for 3 hours.

After then, nanoparticles were obtained by the same method as Example 1 through separation concentration and frozen drying. Upon observing the finally obtained nanoparticles through a particle size analyzer, uniform PLGA-BDD nanoparticles containing active ingredients having narrow bounds of particles distribution and a 152 nm of average particle diameter were confirmed. (Refer to Table 1)

Example 3

Preparation of PLGA-BDD Nanoparticles Using DMF 100 mg of PLGA was dissolved in 3 ml of dimethyl formamide (DMF), and 10 mg of BDD was added on it and dissolved to prepare a dispersion. The above PLGA-BDD dispersion was added on the 30 ml of 4%-PVA emulsifier solution in a batch under the condition of low mechanical energy level stirring at 500 rpm for 3 hours.

After then, nanoparticles were obtained by the same method as Example 1 through separation concentration and frozen drying. Upon observing the finally obtained nanoparticles through a particle size analyzer, uniform PLGA-BDD nanoparticles containing active ingredients having narrow bounds of particles distribution and a 161 nm of average particle diameter were confirmed (Refer to Table 1).

TABLE 1

| Non-volatile polar solvent | DMAc | Deviation (±) | DMSO | Deviation (±) | DMF | Deviation (±) |
|---|---|---|---|---|---|---|
| Average particle diameter (nm) | 142.8 | 3.3 | 152.4 | 4 | 161.6 | 3.3 |

Experimental Example 1

Treatment Effects on Carbon Tetrachloride-Induced Liver Damage

Treatment effects of the polymeric nanoparticles of the present invention containing BDD prepared according to Experiment 2 on carbon tetrachloride-induced liver damage was confirmed via animal tests.

<1-1> Carbon Tetrachloride-Induced Liver Damage 6-week old 20 male Sprague Dawley rats (Orient Bio, Korea) were weighed and distributed to 4 groups 5 to each group to be equal in average weight and degree of dispersion. Under the condition of 23±2'C of temperature and 55±5% of relative humidity in an animal facility, 0.75 ml/kg of 50% solution (v/v) (Sigma-Aldrich, USA) of liver toxic carbon tetrachloride ($CCl_4$) mixed with corn oil was injected each time into the peritoneal cavity 2 times a week (Mondays & Fridays) for 4 weeks.

<1-2> Compounds Treatments

1. For Group 1 (control group), 0.75 ml/kg of carbon tetrachloride was injected each time into the peritoneal cavity 2 times a week (Mondays & Fridays) for 4 weeks, and no additional compounds was administered any more.

2. For Group 2, in addition to the 0.75 ml/kg of carbon tetrachloride injection each time into the peritoneal cavity 2 times a week (Mondays & Fridays) for 4 weeks, BDD equivalent to 25 mg per 1 kg of body weight of each rat, which was suspended in 1% (w/v) of CMC (carboxylmethyl cellulose sodium salt, Sigma-Aldrich, USA) solution were orally administered each time once a day, 6 times a week for 4 weeks.

3. For Group 3, in addition to the 0.75 ml/kg of carbon tetrachloride injection each time into the peritoneal cavity 2 times a week (Mondays & Fridays) for 4 weeks, BDD-containing polymeric nanoparticles of the present invention prepared via Example 2 equivalent to 25 mg per 1 kg of body weight of each rat, which were suspended in 1% (w/v) of CMC (Carboxylmethyl cellulose sodium salt, Sigma-Aldrich, USA) solution were orally administered each time once a day, 6 times a week for 4 weeks.

4. For Group 4 (no treatment group), no carbon tetrachloride and compounds were administered.

<1-3> Confirmation on Treatment Effects

Upon obtaining blood serum after the 4 weeks treatment, concentrations of ALT (alanine aminotransferase, GPT) and AST (aspartate aminotransferase, GOT) were measured to confirm the treatment effects of PLGA-BDD nanoparticles obtained via Experiment 2 of the present invention.

In detail, after 4 weeks, each animal was anesthetized by injecting 4% of 4 ml-chloral hydrate (BDH Laboratory Supplies, U.K.) Into the peritoneal cavity, and blood was taken out from the heart and left at a room temperature for an hour. After then, blood serum was obtained by spinning down at 16000 rpm for 20 minutes, and ALT and AST concentrations were measured by an automatic blood biochemistry analyzer (HITACHI 7080, HITACHI, Japan) using an ALT and AST test reagents (TA-Test Wako; WAKO Pure Chemical, Japan).

As shown in Tables 2 and 3, the inhibiting effect of the BDD and BDD-containing polymeric nanoparticles administration group of the Example 2 on increase of carbon tetrachloride-induced ALT and AST concentration were roughly 2 times or more. The effect of BDD-containing polymeric nanoparticles administration group of the Example 2 was numerically a little lower than that of the BDD administration group but similar. On the other hand, the total administration amount of BDD-containing polymeric nanoparticles of the Example 2 was 25 mg including 2.5 mg of BDD, which means the drug dosage accounts for ¹/₁₀ of the Group 2 which was administered 25 mg of BDD. Examining the results of the Group 3 against the Example 2, it is understood that with the ¹/₁₀ of drug dosage of the Group 2, the effects obtained against the Group 2 reached about 56% (Table 1) and about 91% (Table 2), which means an actual dissolution rate was improved by 5.6 times and 9.1 times, respectively.

TABLE 2

| Animal group | ALT* (SF IU/l) | No. of rats | Relative concentration of ALT against the control group (%) |
|---|---|---|---|
| Group 1 (Control group) | 547.9 ± 26.8 | 5 | 100 |
| Group 2 (BDD) | 229.6 ± 99.7 | 5 | 42 |
| Group 3 (Example 2) | 367.7 ± 45.5 | 5 | 67.1 |
| Group 4 (No treatment) | 54.6 ± 15.4 | 5 | — |

TABLE 2-continued

| Animal group | ALT* (SF IU/l) | No. of rats | Relative concentration of ALT against the control group (%) |
| --- | --- | --- | --- |

*Average value of ALT concentration ± Deviation;
SF: Sigma-Frankel, Activity of enzyme per unit volume

TABLE 3

| Animal group | ALT* (SF IU/l) | No. of rats | Relative concentration of ALT against the control group (%) |
| --- | --- | --- | --- |
| Group 1 (Control group) | 906.6 ± 92.0 | 5 | 100 |
| Group 2 (BDD) | 479.7 ± 144.8 | 5 | 52.9 |
| Group 3 (Example 2) | 516.1 ± 37.0 | 5 | 56.9 |
| Group 4 (No treatment) | 194.3 ± 14.5 | 5 | — |

*Average value of ALT concentration ± Deviation;
SF: Sigma-Frankel, Activity of enzyme per unit volume Experimental Example 2

Prolonged Treatment Effects on Carbon Tetrachloride-Induced Liver Damage

Prolonged treatment effects of BDD-containing polymeric nanoparticles of the present invention prepared via Example 2 on carbon tetrachloride-induced liver damage were confirmed through animal tests. In detail, BDD and BDD containing polymeric nanoparticles of the present invention prepared via Example 2 were administered for 2 weeks, respectively and then, carbon tetrachloride was continuously administered to confirm treatment effects according to the time flow.

<2-1> Carbon Tetrachloride-Induced Liver Damage

Carbon tetrachloride-induced liver damage was conducted on each of 8 groups, 5 rats to each group with the same method as Experimental Example 1-1.

<2-2> Administration of Compounds

1. For Group 1 (control group), 0.75 ml/kg of carbon tetrachloride was injected each time into the peritoneal cavity 2 times a week (Mondays & Fridays) for 4 weeks, and no additional compounds was administered any more.

2. For Group 2, in addition to the 0.75 ml/kg of carbon tetrachloride injection each time into the peritoneal cavity 2 times a week (Mondays & Fridays) for 2 weeks, BDD equivalent to 25 mg per 1 kg of body weight of each rat, which was suspended in 1% (w/v) of CMC solution were orally administered each time once a day, 6 times a week for 2 weeks.

3. For Group 3, in addition to the 0.75 ml/kg of carbon tetrachloride injection each time into the peritoneal cavity 2 times a week (Mondays & Fridays) for 3 weeks, BDD equivalent to 25 mg per 1 kg of body weight of each rat, which was suspended in 1% (w/v) of CMC solution were orally administered each time once a day, 6 times a week for 2 weeks.

4. For Group 4, in addition to the 0.75 ml/kg of carbon tetrachloride injection each time into the peritoneal cavity 2 times a week (Mondays & Fridays) for 4 weeks, BDD equivalent to 25 mg per 1 kg of body weight of each rat, which was suspended in 1% (w/v) of CMC solution were orally administered each time once a day, 6 times a week for 2 weeks.

5. For Group 5, in addition to the 0.75 ml/kg of carbon tetrachloride injection each time into the peritoneal cavity 2 times a week (Mondays & Fridays) for 2 weeks, BDD-containing polymeric nanoparticles of the present invention prepared via Example 1-3 equivalent to 25 mg per 1 kg of body weight of each rat, which was suspended in 1% (w/v) of CMC solution were orally administered each time once a day, 6 times a week for 2 weeks.

6. For Group 6, in addition to the 0.75 ml/kg of carbon tetrachloride injection each time into the peritoneal cavity 2 times a week (Mondays & Fridays) for 3 weeks, BDD equivalent to 25 mg per 1 kg of body weight of each rat, which was suspended in 1% (w/v) of CMC solution were orally administered each time once a day, 6 times a week for 2 weeks.

7. For Group 7, in addition to the 0.75 ml/kg of carbon tetrachloride injection each time into the peritoneal cavity 2 times a week (Mondays & Fridays) for 4 weeks, BDD-containing polymeric nanoparticles of the present invention prepared via Example 2 equivalent to 25 mg per 1 kg of body weight of each rat, which was suspended in 1% (w/v) of CMC solution were orally administered each time once a day, 6 times a week for 2 weeks.

8. For Group 8 (no treatment group), no carbon tetrachloride and compounds were administered.

<2-3> Confirmation on Treatment Effects

After 2 weeks, upon obtaining blood serum after euthanizing each animal every week with the same method as Experimental Example 2, concentrations of ALT and AST were measured to confirm the prolonged treatment effects of PLGA-BDD nanoparticles.

Figure 1:
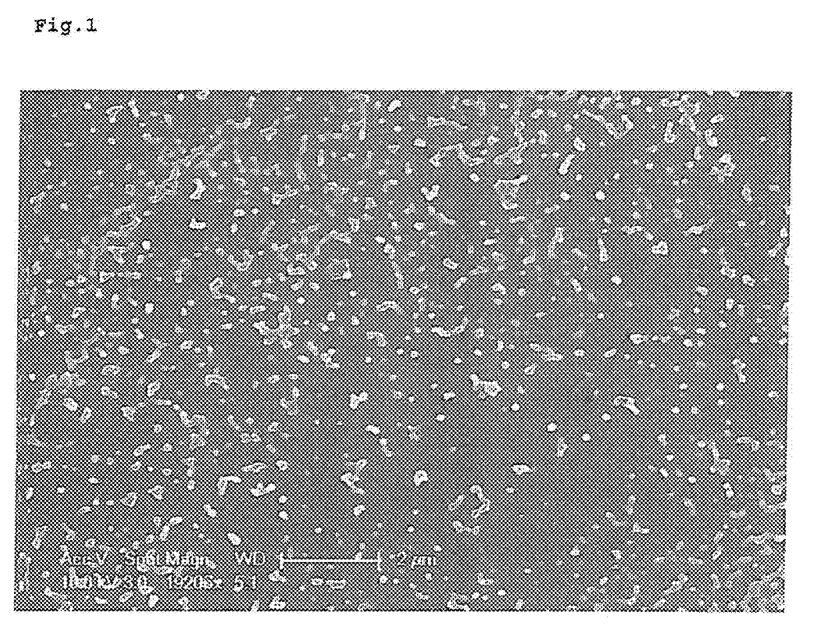
FIG. 1 is a Scanning Electron Microscope (SEM) picture of nanoparticles including poorly soluble BDD which was prepared by using DMAc, a non-volatile polar organic solvent.
Figure 2:
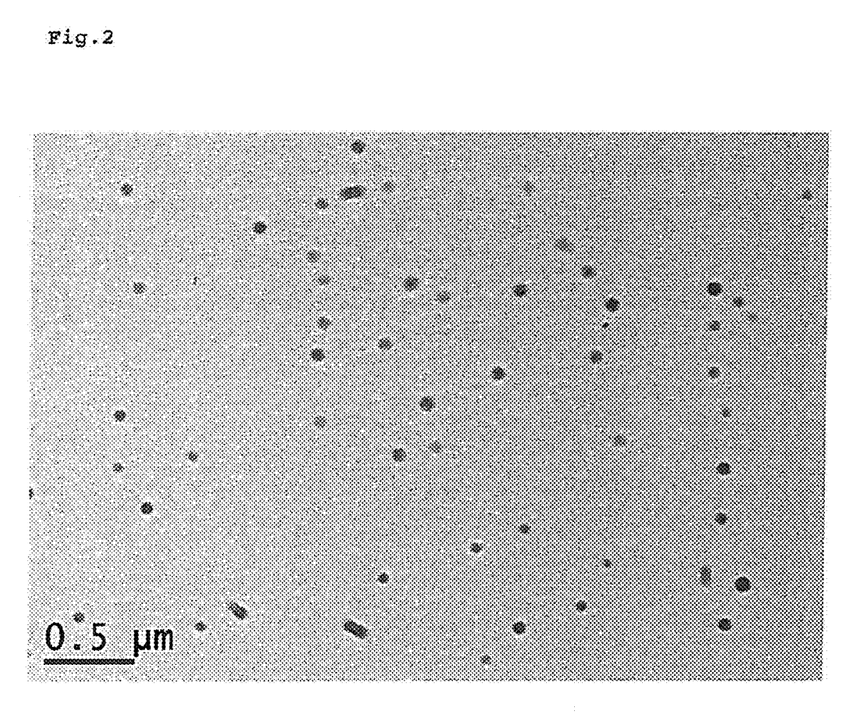
FIG. 2 is a Transmission Electron Microscope (TEM) picture of nanoparticles including poorly soluble BDD which was prepared by using DMAc, a non-volatile polar organic solvent.
Figure 3:
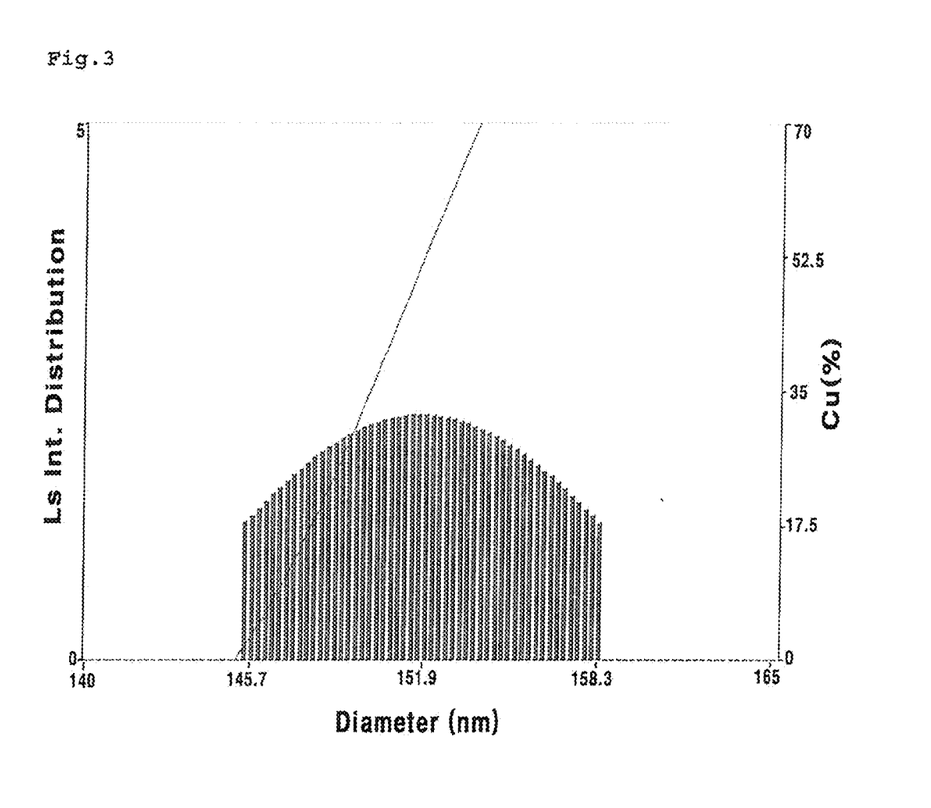
FIG. 3 is a picture of nanoparticles including poorly soluble BDD which was prepared by using DMAc, a non-volatile polar organic solvent.
Figure 4:
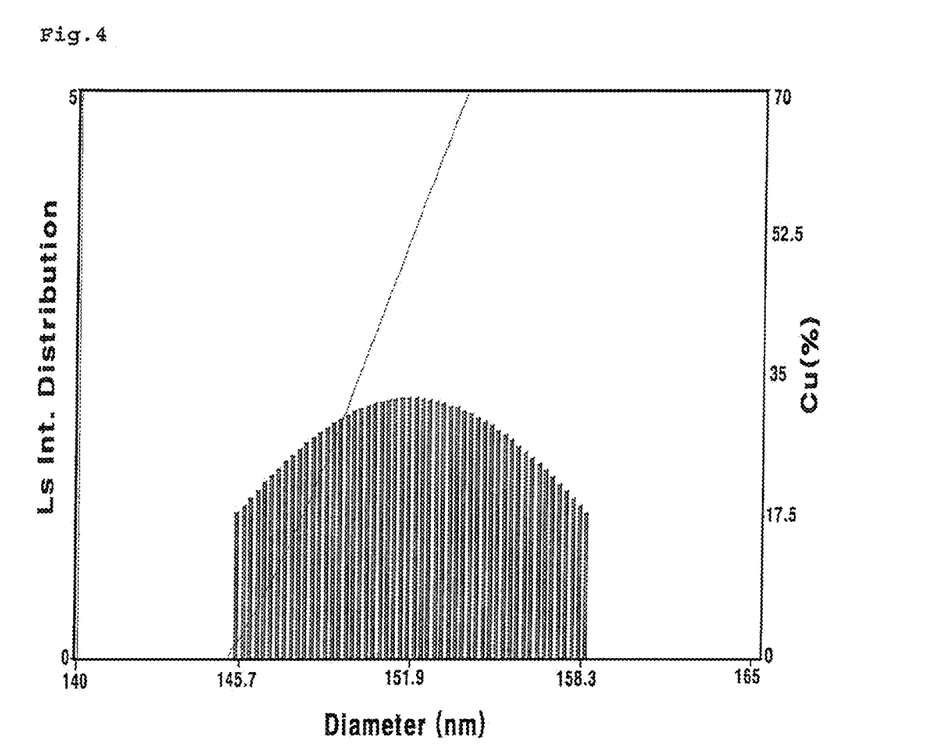
FIG. 4 is a picture illustrating distribution of nanoparticles including poorly soluble BDD which was prepared by using DMSO, a non-volatile polar organic solvent.
Figure 5:
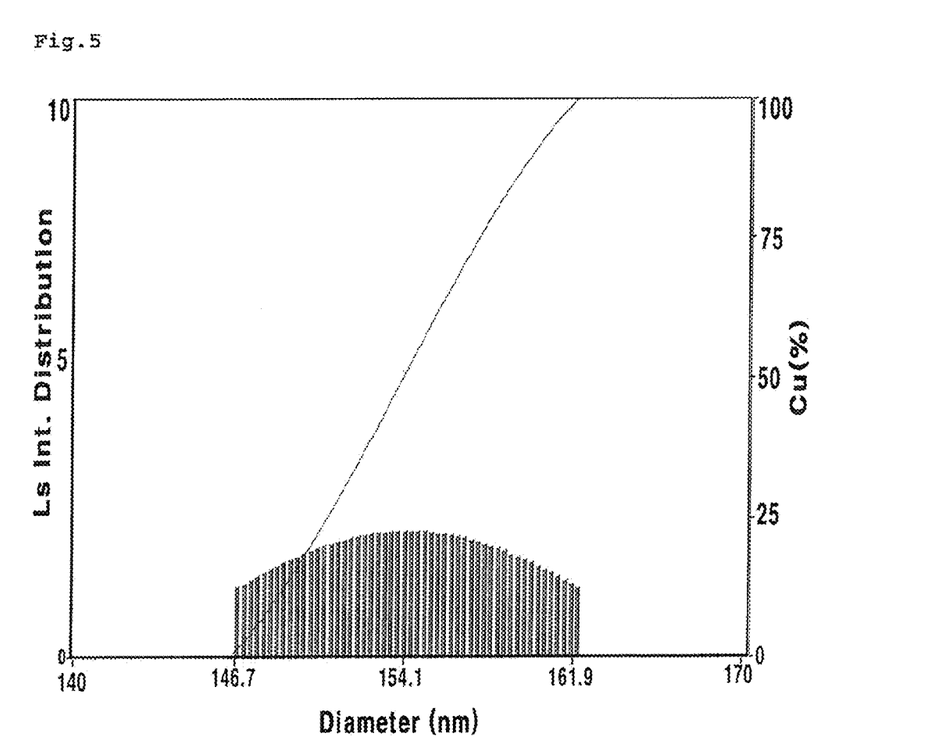
FIG. 5 is a picture illustrating distribution of nanoparticles including poorly soluble BDD which was prepared by using DMF, a non-volatile polar organic solvent.
Figure 6:
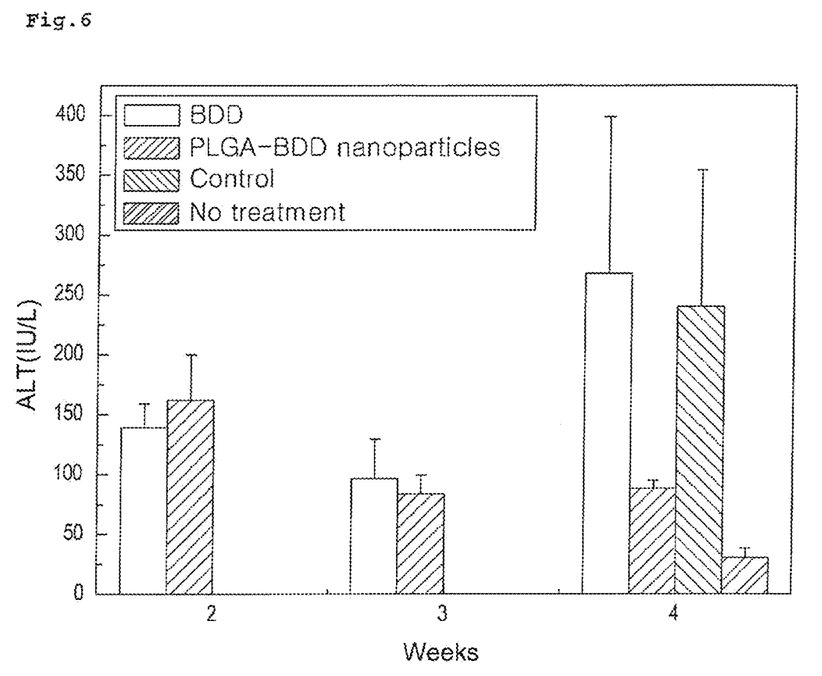
FIG. 6 is a graph showing a lasting treatment effect (by measuring ALT concentration in the liver) of biodegradable polymeric nanoparticles containing BDD of Embodiment 2 of the present invention against the carbon tetrachloride-induced liver damage.
Figure 7:
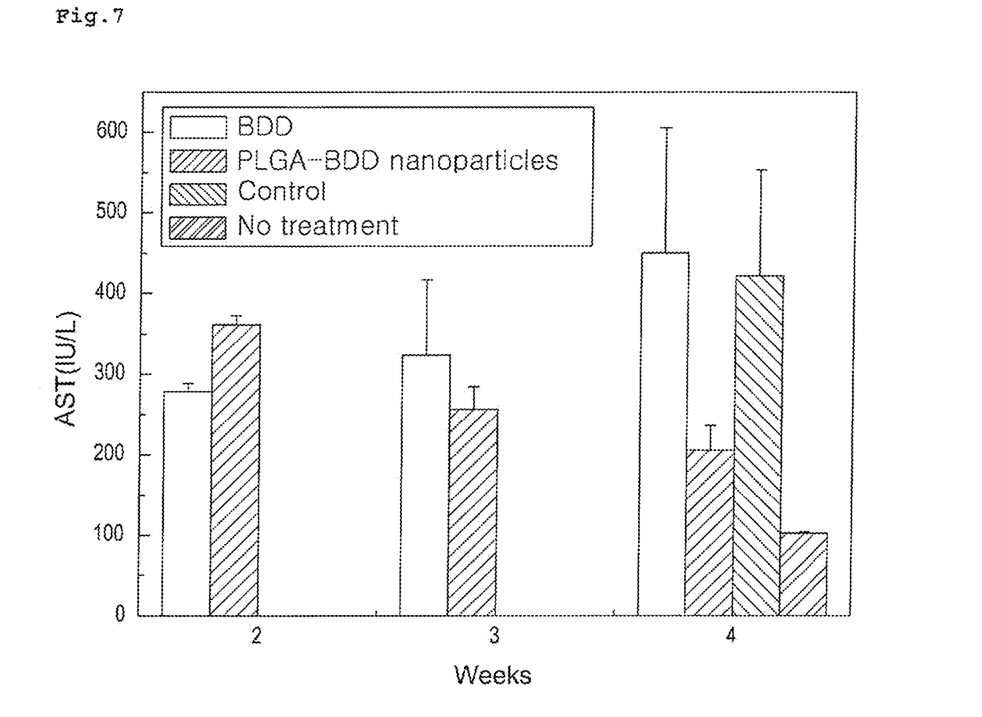
FIG. 7 is a graph showing a lasting treatment effect (by measuring AST concentration in the liver) of biodegradable polymeric nanoparticles containing BDD of Embodiment 2 of the present invention against the carbon tetrachloride-induced liver damage.

As a result, as shown FIGS. 6 and 7, the inhibiting effect of the PLGA-BDD nanoparticles of Example 2 on increase of carbon tetrachloride-induced ALT and AST concentration has been excellent even after 3 and 4 weeks but in case of BDD, the concentration of ALT and AST rebounded after 4 weeks. This result suggests that the dosage form of PLGA-BDD nanoparticles of the present invention prepared via Example 2 help drugs gradually and steadily released and consequently, the treatment effect on liver diseases may be better than BDD-only administration.

Experimental Example 3

Acute Toxicity Test

Acute toxicity was investigated upon administering the PLGA-BDD nanoparticles of the present invention prepared via Example 2.

In detail, 20 to 25 g-weigh 20 ICR rats were distributed to 2 groups, 10 to each group, and BDD and PLGA-BDD nanoparticles of the present invention prepared via Example 2 equivalent to 0.005 g, 0.1 g, 0.25 g, 0.5 g and 1 g per 1 kg of body weight of each rat were orally administered, respectively to measure fatality rates by counting numbers of dead rats after 1 week. As a result, it was confirmed that the administration of PLGA-BDD nanoparticles of the present invention prepared via Example 2 is very safe and toxic-free.

TABLE 4

| | 0.005 g | | 0.1 g | | 0.25 g | | 0.5 g | | 1 g | | |
|---|---|---|---|---|---|---|---|---|---|---|---|
| | No. of dead rats | Fatality rate (%) | No. of dead rats | Fatality rate (%) | No. of dead rats | Fatality rate (%) | No. of dead rats | Fatality rate (%) | No. of dead rats | Fatality rate (%) | $LD_{50}$ (g/kg) >2 |
| BDD | 0 | 0 | 0 | 0 | 0 | 0 | 0 | 0 | 0 | 0 | >2 |
| Ex. 2 | 0 | 0 | 0 | 0 | 0 | 0 | 0 | 0 | 0 | 0 | >2 |

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method for manufacturing uniform size polymeric nanoparticles containing poorly soluble drugs, consisting essentially of:
    a first step of forming a solution of a biodegradable polymer by dissolving a biodegradable polymer in a non-volatile polar organic solvent;
    a second step of forming a drug dispersion by adding poorly soluble drugs in water and to the biodegradable polymer solution obtained from the first step to produce a dispersion;
    a third step of forming polymeric nanoparticles dispersed aqueous solution by adding the dispersion obtained from the second step to an aqueous solution of an emulsifier in a batch with a single stirring at 100-1,000 rpm; and
    a fourth step of removing the organic solvent and water from the nanoparticles dispersed aqueous solution obtained from the third step by using a separation membrane filtration device,
    wherein
    the average size of the polymeric nanoparticles is 200 nm or less;
    the non-volatile polar organic solvent in the first step is selected from the group consisting of dimethyl sulfoxide (DMSO), dimethyl formamide (DMF), Dimethyl acetamide (DMAc), N-methyl-2-pyrrolidone (NMP), pyrrolidone, 1,3-Dimethyl-3,4,5,6-tetrahydro-2(1H)-pyrimidinone (DMPU), hexamethylphosphoramide (HMPA), and a mixture thereof; and
    the emulsifier in the third step is selected from the group consisting of propylene glycol (1,2-dihydroxypropane), polyethylene glycol with a molecular weight of 200 to 600, propylene carbonate (4-methyl-2-oxo-1,3-dioxolane), polyvinyl alcohol (PVA), polyvinyl pyrrolidone (PVP) and mixtures thereof.

2. The method according to claim 1, wherein the biodegradable polymer in the first step is one of or a mixture of two or more polyester-based polymers selected from the group consisting of poly-L-lactic acid (PLA), poly glycolic acid (PGA), poly-D-lactic acid-co-glycolic acid (PLGA), poly-L-lactic acid-co-glycolic acid, poly-D,L-lactic acid-co-glycol acid, poly-caprolactone, poly-valerolacton, poly-hydroxy butyrate and poly-hydroxy valerate.

3. The method according to claim 2, wherein the biodegradable polymer is poly-D-lactic acid-co-glycolic acid (PLGA).

4. The method according to claim 1, wherein the poorly soluble drugs in the second step are selected from the group consisting of griseofulvin, digoxin, dipyridamole, spironolactone, cyclosporin, amphotericin B, fluorouracil, etoposide, 6-mercaptopurine, dexamethasone, perphenasine, biphenyl-dimethyl-dicarboxylate (BDD) and dimethyl dimethoxy biphenyl dicarboxylate (DDB).

5. The method according to claim 1, wherein the poorly soluble drugs in the dispersion exist in the oil or crystal phase.

6. The method according to claim 1, wherein the polymeric nanoparticles prepared thereby are uniform size polymeric nanoparticles having a deviation in size of 0-30 nm.

* * * * *